(12) United States Patent
Konishi et al.

(10) Patent No.: US 11,547,643 B2
(45) Date of Patent: Jan. 10, 2023

(54) WATER-IN-OIL EMULSION-TYPE STICK-SHAPED DEODORANT COMPOSITION

(71) Applicant: SHIN-ETSU CHEMICAL CO., LTD., Tokyo (JP)

(72) Inventors: Masayuki Konishi, Tokyo (JP); Ryuichi Inaba, Tokyo (JP)

(73) Assignee: SHTN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 16/643,005

(22) PCT Filed: Aug. 21, 2018

(86) PCT No.: PCT/JP2018/030809
§ 371 (c)(1),
(2) Date: Feb. 28, 2020

(87) PCT Pub. No.: WO2019/044590
PCT Pub. Date: Mar. 7, 2019

(65) Prior Publication Data
US 2020/0253843 A1 Aug. 13, 2020

(30) Foreign Application Priority Data
Aug. 30, 2017 (JP) .............................. JP2017-165509

(51) Int. Cl.
| | |
|---|---|
| *A61K 8/06* | (2006.01) |
| *A61K 8/02* | (2006.01) |
| *A61K 8/26* | (2006.01) |
| *A61K 8/27* | (2006.01) |
| *A61K 8/28* | (2006.01) |
| *A61K 8/34* | (2006.01) |
| *A61K 8/368* | (2006.01) |
| *A61K 8/41* | (2006.01) |
| *A61K 8/43* | (2006.01) |
| *A61K 8/60* | (2006.01) |
| *A61K 8/891* | (2006.01) |
| *A61K 8/92* | (2006.01) |
| *A61K 8/96* | (2006.01) |
| *A61Q 15/00* | (2006.01) |

(52) U.S. Cl.
CPC ............ *A61K 8/064* (2013.01); *A61K 8/0229* (2013.01); *A61K 8/26* (2013.01); *A61K 8/27* (2013.01); *A61K 8/28* (2013.01); *A61K 8/342* (2013.01); *A61K 8/347* (2013.01); *A61K 8/368* (2013.01); *A61K 8/416* (2013.01); *A61K 8/43* (2013.01); *A61K 8/602* (2013.01); *A61K 8/891* (2013.01); *A61K 8/92* (2013.01); *A61K 8/96* (2013.01); *A61Q 15/00* (2013.01); *A61K 2800/77* (2013.01)

(58) Field of Classification Search
None
See application file for complete search history.

(56) References Cited

U.S. PATENT DOCUMENTS

| | | | |
|---|---|---|---|
| 6,139,824 | A | 10/2000 | Ribery et al. |
| 7,037,511 | B1 | 5/2006 | Gers-Barlag et al. |
| 2010/0158834 | A1 | 6/2010 | Falk |
| 2011/0212144 | A1 | 9/2011 | Lemoine et al. |
| 2014/0364394 | A1 | 12/2014 | Tamura et al. |
| 2016/0220463 | A1 | 8/2016 | Cropper et al. |

FOREIGN PATENT DOCUMENTS

| | | |
|---|---|---|
| JP | 2000-72640 A | 3/2000 |
| JP | 2001-72528 A | 3/2001 |
| JP | 2001-503039 A | 3/2001 |
| JP | 2005-179305 A | 7/2005 |
| JP | 2005-314258 A | 11/2005 |
| JP | 2013-151660 A | 8/2013 |
| JP | 2015-3891 A | 1/2015 |
| JP | 2016-216516 A | 12/2016 |
| JP | 6058201 B2 | 1/2017 |
| WO | WO 2010/080482 A2 | 7/2010 |

OTHER PUBLICATIONS

International Search Report, issued in PCT/JP2018/030809, dated Sep. 25, 2018.
New Cosmetics, Nanzando, 2001, pp. 510-515.
Written Opinion of the International Searching Authority, issued in PCT/JP2018/030809, dated Sep. 25, 2018.

*Primary Examiner* — Jessica Worsham

(74) *Attorney, Agent, or Firm* — Birch, Stewart, Kolasch & Birch, LLP

(57) ABSTRACT

This water-in-oil emulsion-type stick-shaped deodorant composition contains: (A) a volatile component having a boiling point of 250° C. or less, where the total amount of water and ethanol in the (A) component is 83-100 mass %; (B) component (B-1), component (B-2), or a combination of components (B-1) and (B-2), wherein component (B-1) is an antiperspirant and component (B-2) is a fungicide; (C) a crosslinked silicone surfactant; (D) a non-crosslinked silicone surfactant; and (E) an oily component which has a solid phase at 25° C.

9 Claims, No Drawings

WATER-IN-OIL EMULSION-TYPE STICK-SHAPED DEODORANT COMPOSITION

TECHNICAL FIELD

This invention relates to a water-in-oil emulsion type stick-shaped deodorant composition with good portability.

BACKGROUND ART

Deodorant agents are compositions intended to prevent body odor. It is known that body odor is produced by the bacterial interaction on the body surface with sweat and sebum secreted from the human body. Therefore, the known means for preventing body odor include, for example, a method of using bactericides or fungicides to control bacteria on the body surface, a method of using antiperspirants such as metal oxides to control secretion of sweat, a method of using antioxidants such as plant extracts to control oxidation of sebum, a method of using basic substances such as zinc oxide to form complexes with lower fatty acids which can cause body odor, to control body odor, a method of using fragrant substances to mask body odor, and the like. See Non-Patent Document 1.

Since deodorant agents are typically applied to profusely sweating parts and frequently used in heavily sweating season, it is often required that the deodorant product gives a dry feeling when applied to the skin. Typical of the means for developing a dry feeling is blending of silicone having a high volatility rate. As the general-purpose highly volatile substance, octamethylcyclotetrasiloxane, decamethylcyclopentasiloxane and the like are selected. For the purpose of controlling the volatility rate, Patent Document 1 (WO 2010/080482) discloses a cosmetic composition comprising a blend of at least two cycloalkylmethicones having different volatility rates. The technology describes one exemplary non-aqueous solid antiperspirant. When it is intended to develop a dry feeling by blending a large amount of a highly volatile silicone as in Example, a strong dry feeling may be perceived when the deodorant agent is applied. When the deodorant agent is applied to the skin, quick volatilization of oily substances can occur so that the oil composition of the deodorant agent on the skin may change rapidly, that is, the relative ratio of non-volatile oil component may increase to invite a quick viscosity buildup, eventually causing an uncomfortable feeling like sticky feeling.

On the other hand, Patent Document 2: JP 6058201 proposes an emulsion type deodorant stick. The technology describes an emulsion type deodorant stick wherein purified water, distilled water, ion exchange water, hot spring water or deep ocean water is blended as the water component, preferably in an amount of up to 25% by weight based on the total weight of the deodorant. In all examples, decamethylcyclopentasiloxane is selected in order to develop a dry feeling.

PRIOR ART DOCUMENTS

Patent Documents

Patent Document 1: WO 2010/080482
Patent Document 2: JP 6058201

Non-Patent Document

Non-Patent Document 1: New Cosmetics, Nanzando, 2001, p. 510-515

SUMMARY OF INVENTION

Technical Problem

While the invention has been made under the above-mentioned circumstances, with a focus on an excessive dry feeling and a fresh feeling on use of a deodorant composition intended to prevent uncomfortable body odor, an object is to provide a water-in-oil emulsion type stick-shaped deodorant composition which is able to impart a fresh feeling on use without causing an excessive dry feeling, and has improved perspiration resistance (water resistance), non-sticky convenient use and spread, anti-stick-thinning and collapsing properties, product stability, and portability.

Solution to Problem

Making extensive investigations to attain the above object, the inventors have found that by using water or ethanol as the majority of volatile component (A), it is possible to avoid an excessive dry feeling which is brought about on use of volatile silicone as in the prior art products, to impart a fresh feeling on use, and to mitigate stick thinning, and by further incorporating components (B) to (E) to water-in-oil emulsion type formulation, there is obtained a stick-shaped deodorant composition having perspiration resistance (water resistance), convenient use and spread, product stability, anti-stick-collapsing properties, and portability. The invention is predicated on this finding.

Accordingly, the invention is as defined below.

[1] A water-in-oil emulsion type stick-shaped deodorant composition comprising
(A) 30 to 70% by weight of a volatile component having a boiling point of up to 250° C., the total of water and ethanol in component (A) being 83 to 100% by weight,
(B) either one of (B-1) an antiperspirant and (B-2) a bactericide, or a combination of (B-1) and (B-2),
(C) a crosslinked silicone surfactant,
(D) a non-crosslinked silicone surfactant, and
(E) an oily component which is solid at 25° C.

[2] The stick-shaped deodorant composition of [1] wherein component (B-1) is at least one antiperspirant selected from the group consisting of aluminum hydrochloride, allantoin aluminum hydrochloride, aluminum chloride, allantoin aluminum salt, tannic acid, persimmon tannin, aluminum potassium sulfate, zinc oxide, zinc p-phenol sulfonate, dry aluminum potassium sulfate, aluminum zirconium tetrachlorohydrate, and aluminum zirconium trichlorohydrex gly.

[3] The stick-shaped deodorant composition of [1] or [2] wherein component (B-2) is at least one bactericide selected from the group consisting of triclosan, benzalkonium chloride, benzethonium chloride, chlorhexidine hydrochloride, chlorhexidine gluconate, cloflucarban, isopropyl methyl phenol, and salicylic acid.

[4] The stick-shaped deodorant composition of any one of [1] to [3] wherein component (E) is at least one oily component selected from the group consisting of carnauba wax, candelilla wax, rice wax, Japan wax, beeswax, spermaceti, solid paraffin, polyethylene, ceresin, ozokerite, microcrystalline wax, synthetic wax, stearyl alcohol, behenyl alcohol, cetanol, stearic acid, behenic acid, and silicone wax.

[5] The stick-shaped deodorant composition of any one of [1] to [4] wherein the amount of component (B-1) blended is 0.1 to 30% by weight when it is used, the amount of component (B-2) blended is 0.05 to 2% by weight when it is used, the amount of component (C) blended is 0.15 to 3% by weight, and the amount of component (D) blended is 0.1 to 10% by weight, based on the deodorant composition.

ADVANTAGEOUS EFFECTS OF INVENTION

The invention provides a water-in-oil emulsion type stick-shaped deodorant composition which is able to impart a fresh feeling on use without causing an excessive dry feeling, and has improved perspiration resistance (water resistance), non-sticky convenient use and spread, anti-stick-thinning and collapsing properties, product stability, and portability.

DESCRIPTION OF EMBODIMENTS

Now the invention is described in detail.
[Component (A)]
Component (A) is not particularly limited as long as it is a volatile component having a boiling point of up to 250° C. Component (A) may be used alone or in a suitable combination of two or more. Examples include oily volatile components such as dimethylpolysiloxanes having a boiling point of up to 250° C. (KF-96L-1cs, KF-96L-1.5cs, KF-96L-2cs, etc., from Shin-Etsu Chemical Co., Ltd.), octamethyltetrasiloxane (D4), decamethylpentasiloxane (KF-995 (D5), from Shin-Etsu Chemical Co., Ltd.), dodecamethylhexasiloxane (D6), tristrimethylsiloxymethylsilane (TMF-1.5, from Shin-Etsu Chemical Co., Ltd.), caprylyl methicone, decamethylcyclopentasiloxane, soft isoparaffin, undecane, and isododecane, and aqueous volatile components such as water, ethanol, and isopropyl alcohol. Herein purified water, distilled water, ion exchange water, hot spring water, deep ocean water, and distilled water from fruits and plants may be used as the water.

The amount of component (A) blended is 30 to 70% by weight of the water-in-oil emulsion type stick-shaped deodorant composition (sometimes abbreviated as deodorant composition, hereinafter). The range of component (A) blended ensures that when the deodorant composition is applied, component (A) volatilizes off the deodorant composition, leaving a dry feeling. When it is desired to impart a more dry feeling, component (A) is preferably blended in an amount of 50 to 70% by weight. Further the total of water and ethanol in component (A) is 83 to 100% by weight, preferably 90 to 100% by weight, and most preferably 100% by weight, indicating exclusion of oily volatile components. If the total of water and ethanol is less than 83% by weight, it is likely that an excessive dry feeling is perceived, no fresh feeling on use is obtainable, and sticks thin down.
[Component (B)]
Component (B) is either one of (B-1) and (B-2), or a combination of (B-1) and (B-2), defined below.
(B-1) Antiperspirant
The antiperspirant is not particularly limited as long as it suppresses perspiration by astringing the skin. A choice may be made from a wide variety of commonly used ingredients. These ingredients may be used alone or in suitable combination of two or more. Examples of the antiperspirant include aluminum hydrohalides such as aluminum hydrochloride and allantoin aluminum hydrochloride, aluminum halides such as aluminum chloride, allantoin aluminum salts, tannic acid, persimmon tannin, aluminum potassium sulfate, zinc oxide, zinc p-phenol sulfonate, dry aluminum potassium sulfate, aluminum zirconium tetrachlorohydrate, and aluminum zirconium trichlorohydrex gly. Of these, aluminum hydrohalides, aluminum halides, and complexes thereof with zirconyl oxyhalide or zirconyl hydrohalide, or mixtures thereof, e.g., aluminum zirconium tetrachlorohydrate and aluminum zirconium trichlorohydrex gly are preferred as the component exerting a better effect. On use, these antiperspirants may be blended in deodorant compositions, after dissolving in water or directly in powder form. Also commercial products may be used. The commercial product of choice may be in the form of a mixture of the relevant component with another component.

When component (B-1) is blended, the amount of component (B-1) blended is preferably 0.1 to 30% by weight, more preferably 0.2 to 20% by weight of the deodorant composition for the purpose of obtaining a deodorant composition having an excellent antiperspirant effect and for the purpose of obtaining a deodorant composition which is less stimulating to the skin.
(B-2) Bactericide
The bactericide is not particularly limited as long as it achieves a deodorant effect by restraining the multiplication of resident skin bacteria producing body odor-causing substances. Suitable ingredients may be used alone or in suitable combination of two or more. As the bactericide, bactericidal agents such as triclosan, benzalkonium chloride, benzethonium chloride, chlorhexidine hydrochloride, chlorhexidine gluconate, cloflucarban, isopropyl methyl phenol, and salicylic acid are generally used. Also useful are essential oils and extracts originating from crude drugs and having bactericidal property such as green tea extracts by dry distillation. Useful bactericides having a deodorant effect like essential oils and extracts originating from crude drugs include, for example, green tea extract, lavender extract, scutellaria root extract, coptis rhizome extract, phellodendron bark extract, artemisia capillaris extract, candelabra aloe extract, shrubby sophora extract, sasa veitchii extract, garlic extract, witch-hazel extract, black tea extract, common sage leaf extract, Japanese pepper extract, ginger root extract, acorns calamus root extract, hedera helix extract, chameleon plant extract, peach fruit extract, peach leaf extract, peppermint leaf extract, cnidium officinale root extract, eucalyptus globulus leaf extract, peanut seedcoat extract, mushroom extract, sanguisorba officinalis root extract, etc. The plant extracts may be used alone or in suitable combination of two or more. Inter alia, preference is given to triclosan, benzalkonium chloride, benzethonium chloride, chlorhexidine hydrochloride, chlorhexidine gluconate, cloflucarban, isopropyl methyl phenol, and salicylic acid.

When component (B-2) is blended, the amount of the bactericide blended is preferably 0.05 to 2% by weight, more preferably 0.1 to 1.5% by weight of the deodorant composition for the purpose of obtaining a deodorant composition having an excellent bactericidal effect and for the purpose of obtaining a deodorant composition which is less stimulating to the skin.
[Component (C)]
The crosslinked silicone surfactant is blended for obtaining a stable water-in-oil type emulsion composition and may be used alone or in suitable combination of two or more. Typical of the crosslinked silicone surfactant are partially crosslinked polyether-modified silicones and partially crosslinked polyglycerol-modified silicones. In these surfactants, the content of hydrophilic polyoxyethylene group, polyoxyethylene polyoxypropylene group or polyglycerol residue is preferably 10 to 70% by weight of the molecule. Also on use of the partially crosslinked polyether-modified silicone or partially crosslinked polyglycerol-modified silicone, it is preferred that in a composition comprising the crosslinked organopolysiloxane and a normally liquid oil, the crosslinked organopolysiloxane is swollen with the liquid oil by taking up the liquid oil in an amount of equal to or more than its own weight. The liquid oil may be cycloalkylmethicone, or a liquid silicone corresponding to component (A), hydrocarbon oil, ester, natural animal or plant oil, semi-synthetic oil or fluorochemical oil may be used. Specific examples of the liquid oil include silicones having a low viscosity of 0.65 to 100 mm$^2$/s (as measured at 25° C. by an Ostwald viscometer, the same holds true, hereinafter), hydrocarbon oils such as liquid paraffin, squalane, isododecane, and isohexadecane, glyceride oils such as trioctanoin, esters such as isotridecyl isononanoate, N-acylglutamic acid esters, lauroyl sarcosine esters, natural animal or plant oils such as macadamia nut oil and jojoba oil.

Examples of the partially crosslinked polyether-modified silicone include KSG-210, 240, 310, 320, 330, 340, 320Z and 350Z from Shin-Etsu Chemical Co., Ltd. Examples of the partially crosslinked polyglycerol-modified silicone include KSG-710, 810, 820, 830, 840, 820Z and 850Z from Shin-Etsu Chemical Co., Ltd.

The amount of component (C) blended is preferably 0.15 to 3.0% by weight, more preferably 0.2 to 2.5% by weight of the deodorant composition. At least 0.15% by weight of component (C) is effective for a dispersing or emulsifying function to develop more. More than 3.0% by weight can cause the deodorant composition to develop a sticky feeling on use.

[Component (D)]

The non-crosslinked silicone surfactant is a surfactant other than the crosslinked silicone surfactant and may be used alone or in suitable combination of two or more. By using the non-crosslinked silicone surfactant in combination with the crosslinked silicone surfactant (C), a more stable water-in-oil type emulsion composition is obtainable. Examples of the non-crosslinked silicone surfactant include linear or branched polyoxyethylene-modified organopolysiloxanes, linear or branched polyoxyethylene polyoxypropylene-modified organopolysiloxanes, linear or branched polyoxyethylene/alkyl-co-modified organopolysiloxanes, linear or branched polyoxyethylene polyoxypropylene/alkyl-co-modified organopolysiloxanes, linear or branched polyglycerol-modified organopolysiloxanes, and linear or branched polyglycerol/alkyl-co-modified organopolysiloxanes.

Specific examples include polyether-modified silicones such as KF-6011, 6013, 6043, 6017, 6017(P), silicone-branched polyether-modified silicones such as KF-6028, 6028(P), silicone-branched polyglycerol-modified silicones such as KF-6100, 6104, 6106, acrylic silicone base graft copolymers such as KP-578, all from Shin-Etsu Chemical Co., Ltd. Especially, surfactants having alkyl branches on the backbone are more preferred because of good compatibility with component (E), for example, linear or branched polyoxyethylene/alkyl-co-modified organopolysiloxanes and linear or branched polyoxyethylene polyoxypropylene/alkyl-co-modified organopolysiloxanes. Specific examples include silicone/alkyl-branched polyether-modified silicones such as KF-6038, alkyl-branched polyether-modified silicones such as KF-6048, silicone/alkyl-branched polyglycerol-modified silicones such as KF-6105, all from Shin-Etsu Chemical Co., Ltd.

The amount of component (D) blended is preferably 0.1 to 10% by weight, more preferably 0.1 to 6% by weight of the deodorant composition. At least 0.1% by weight of component (D) is effective for a dispersing or emulsifying function to develop more. More than 10% by weight can cause the deodorant composition to develop a sticky feeling on use.

It is noted that surfactants as components (C) and (D) should preferably have a HLB of 2 to 14.5, though not limitative, for the purpose of maintaining the product water resistant. HLB is determined by Griffin's method.

[Component (E)]

In the inventive, the oily component which is solid at 25° C. is blended in order that the deodorant composition is solidified into a stick shape with portability. The oily component is not particularly limited as long as it is solid at 25° C. and may be used alone or in suitable combination of two or more. The oily component which is solid at 25° C. is preferably selected from compounds having a melting point of at least 40° C., more preferably 60 to 110° C., for example, waxes, hydrocarbons, esters, higher alcohols, and higher fatty acids. These compounds are not particularly limited as long as they are normally allowed to be included in deodorant compositions. Examples include plant waxes such as carnauba wax, candelilla wax, rice wax, and Japan wax, animal waxes such as beeswax and spermaceti, hydrocarbon waxes such as solid paraffin, polyethylene, ceresin, ozokerite, microcrystalline wax, and synthetic wax, higher alcohols such as stearyl alcohol, behenyl alcohol, and cetanol, fatty acids such as stearic acid and behenic acid, and silicone waxes such as acrylic silicone resins in the form of acrylic silicone graft or block copolymers (e.g., acrylic silicone graft copolymers KP-561P, 562P from Shin-Etsu Chemical Co., Ltd.), and derivatives thereof.

The amount of component (E) blended is preferably 1 to 18% by weight, more preferably 2 to 15% by weight of the deodorant composition. At least 1% by weight of component (E) facilitates to shape the composition into sticks. If the amount exceeds 18% by weight, the deodorant composition may become too hard to apply to the skin.

[Optional Components]

Besides the foregoing components (A) to (E), a variety of optional components commonly used in deodorant compositions may be blended in the deodorant composition of the invention as long as the benefits of the invention are not compromised. Suitable optional components include, for example, (1) oils (exclusive of components (A) and (E)), (2) compounds having an alcoholic hydroxyl group (exclusive of component (A)), (3) surfactants other than components (C) and (D), (4) powders, (5) compositions consisting of a crosslinked organopolysiloxane (exclusive of component (C)) and a normally liquid oil, (6) film-forming agents, and (7) other additives. These components may be used alone or in suitable combination of two or more and in adequate amounts.

(1) Oil (Exclusive of Components (A) and (E))

The oils exclusive of components (A) and (E) may be either semi-solid or liquid. For example, use may be made of naturally occurring animal/plant oils and fats, semi-synthetic oils and fats, hydrocarbon oils, esters, cycloalkylmethicones, silicone oils, and fluorochemical oils.

Naturally Occurring Animal/Plant Oils and Fats and Semi-Synthetic Oils and Fats

Suitable naturally occurring animal/plant oils and fats and semi-synthetic oils and fats include avocado oil, linseed oil, almond oil, insect wax, perilla oil, olive oil, cacao butter, kapok oil, kaya oil, liver oil, apricot kernel oil, hydrogenated oil, wheat germ oil, sesame oil, rice germ oil, rice bran oil, sugar cane wax, sasanqua oil, safflower oil, shea butter, Chinese tung oil, cinnamon oil, jojoba wax, squalane, squalene, shellac wax, turtle oil, soybean oil, tea seed oil, tsubaki oil, evening primrose oil, corn oil, rape oil, Japanese tung oil, wheat germ oil, persic oil, palm oil, palm kernel oil, castor oil, hydrogenated castor oil, castor oil fatty acid methyl ester, sunflower oil, grape seed oil, bay oil, jojoba oil, macadamia nut oil, mink oil, meadowfoam seed oil, cotton seed oil, coconut oil, hydrogenated coconut oil, tri-coconut oil fatty acid glyceride, beef tallow, peanut oil, lanolin, liquid lanolin, reduced lanolin, lanolin alcohol, hard lanolin, lanolin acetate, lanoline acetate alcohol, lanolin fatty acid isopropyl, polyoxyethylene lanolin alcohol ether, polyoxyethylene lanolin alcohol acetate, lanolin fatty acid polyethylene glycol, polyoxyethylene hydrogenated lanolin alcohol ether, and egg yolk oil.

Hydrocarbon Oils

Suitable hydrocarbon oils include linear and branched hydrocarbon oils which may be volatile or non-volatile. Specific examples include α-olefin oligomers, light liquid isoparaffin, squalane, synthetic squalane, plant squalane, squalene, liquid paraffin, liquid isoparaffin, polyisobutylene, hydrogenated polyisobutene, and vaseline.

Higher Fatty Acids

Suitable higher fatty acids include oleic acid, linoleic acid, linolenic acid, arachidic acid, eicosapentaenoic acid (EPA), docosahexaenoic acid (DHA), isostearic acid, and 12-hydroxystearic acid.

Esters

Suitable esters include diisobutyl adipate, 2-hexyldecyl adipate, di-2-heptylundecyl adipate, N-alkylglycol monoisostearate, isocetyl isostearate, trimethylol propane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, neopentyl glycol dioctanoate, neopentyl glycol dicaprylate, triethyl citrate, 2-ethylhexyl succinate, amyl acetate, ethyl acetate, butyl acetate, isocetyl stearate, butyl stearate, diisopropyl sebacate, di-2-ethylhexyl sebacate, cetyl lactate, myristyl lactate, isononyl isononanoate, isotridecyl isononanoate, isopropyl palmitate, 2-ethylhexyl palmitate, 2-hexyldecyl palmitate, 2-heptylundecyl palmitate, cholesteryl 12-hydroxystearate, dipentaerythritol fatty acid ester, isopropyl myristate, octyldodecyl myristate, 2-hexyldecyl myristate, myristyl myristate, hexyldecyl dimethyloctanoate, ethyl laurate, hexyl laurate, 2-octyldodecyl N-lauroyl-L-glutamate, lauroyl sarcosine isopropyl ester, diisostearyl malate; glyceride oils such as acetoglyceryl, glyceryl triisooctanoate, glyceryl triisostearate, glyceryl triisopalmitate, glyceryl tribehenate, glyceryl monostearate, glyceryl di-2-heptylundecanoate, glyceryl trimyristate, and diglyceryl myristate isostearate.

Silicone Oils

As the silicone oil, cycloalkylmethicones and silicone oils other than component (A) which is essential for the invention to exert the desired effects may be blended. Examples include dimethylpolysiloxanes (nonvolatile ones with 6 cs or higher), phenyltrimethicone, methylphenylpolysiloxane (KF-54, KF-54HV from Shin-Etsu Chemical Co., Ltd.), diphenylsiloxyphenyltrimethicone (KF-56A from Shin-Etsu Chemical Co., Ltd.), linear or branched organopolysiloxanes from a low viscosity to a high viscosity such as methylhexylpolysiloxane, methylhydrogenpolysiloxane, and dimethyl siloxane-methylphenylsiloxane copolymers, amino-modified organopolysiloxanes, pyrrolidone-modified organopolysiloxanes, pyrrolidone carboxylic acid-modified organopolysiloxanes, silicone rubbers such as gum-like dimethylpolysiloxane having a high degree of polymerization, gum-like amino-modified organopolysiloxanes, gum-like dimethyl siloxane-methylphenylsiloxane copolymers, and cyclic organopolysiloxane solutions of silicone gum or rubber, solutions of amino acid-modified silicones, fluorine-modified silicones, and silicone resins.

Fluorochemical Oils

Suitable Fluorochemical Oils Include Perfluoropolyether, Perfluorodecalin, and Perfluorooctane.

(2) Compound having Alcoholic Hydroxyl Group, Exclusive of Component (A)

Suitable compounds having an alcoholic hydroxyl group, exclusive of component (A), are sucrose alcohols such as sorbitol and maltose. Also useful are sterols such as cholesterol, sitosterol, phytosterol, and lanosterol, and polyhydric alcohols such as butylene glycol, propylene glycol, glycerol, dibutylene glycol, and pentylene glycol.

(3) Surfactant other than Components (C) and (D)

Suitable surfactants other than components (C) and (D) include nonionic, anionic, cationic, and ampholytic surfactants, but are not limited. Any of surfactants commonly included in deodorant compositions may be used.

(4) Powder

Suitable powders include coloring pigments, inorganic powders, metal powders, organic powders, and inorganic/organic composite powders. Examples are shown below.

Coloring Pigments

The coloring pigment is not particularly limited as long as it is commonly used for the purpose of coloring products. Examples include red iron oxide, yellow iron oxide, white titanium oxide, black iron oxide, red iron oxide, Prussian blue, ultramarine, manganese violet, cobalt violet, chromium hydroxide, chromium oxide, cobalt oxide, cobalt titanate, iron oxide-doped titanium oxide, iron titanate, fired titanium/titanium oxide, lithium/cobalt titanate, cobalt titanate, titanium nitride, iron hydroxide, brown inorganic pigments such as γ-iron oxide, yellow inorganic pigments such as yellow ochre, color pigments such as lake form tar dyes and lake form natural dyes. Any of these may be used. Also the pigment may be of any shape including spherical, generally spherical, rod, spindle, petal, strip, and irregular shapes. The geometrical form of the pigment is not particularly limited as long as it can impart a color to the preparation.

Inorganic Powder

Suitable inorganic powders include microparticles of zirconium oxide, cerium oxide, magnesium oxide, barium sulfate, calcium sulfate, magnesium sulfate, calcium carbonate, magnesium carbonate, talc, phyllosilicate, kaolin, sericite, mica, synthetic mica, muscovite, phlogopite, lepidolite, biotite, silicic acid, silicon dioxide, fumed silica, hydrous silicon dioxide, aluminum silicate, magnesium silicate, aluminum magnesium silicate, calcium silicate, barium silicate, strontium silicate, metal tungstates, hydroxyapatite, vermiculite, Higilite, bentonite, montmorillonite, hectorite, zeolite, ceramic powder, calcium secondary phosphate, alumina, aluminum hydroxide, boron nitride, and glass. Suitable inorganic pearlescent pigments include titania-coated mica, bismuth oxychloride, titania-coated bismuth oxychloride, titania-coated talc, fish scale flake, and titania-coated colored mica.

Metal Powder

Suitable metal powders include microparticles of aluminum, copper, stainless steel, silver, etc.

Organic Powder

Suitable organic powders include, for example, powders of silicone, polyamide, polyacrylic acid-acrylate, polyester, polyethylene, polypropylene, polystyrene, styrene-acrylic acid copolymers, divinylbenzene-styrene copolymers, polyurethane, vinyl resins, urea resins, melamine resins, benzoguanamine, polymethyl benzoguanamine, tetrafluoroethylene, polymethyl methacrylate (e.g., polymethyl methacrylate), cellulose, silk, nylon, phenolic resins, epoxy resins, polycarbonate, etc. Specifically, suitable silicones include silicone resin particles (e.g., KMP-590, 591, etc. from Shin-Etsu Chemical Co., Ltd.), and silicone resin-coated silicone rubber powders (e.g., KSP-100, 101, 102, 105, 300, 411, 441, etc. from Shin-Etsu Chemical Co., Ltd.). Also metal soaps are useful, and examples thereof include powders of zinc stearate, aluminum stearate, calcium stearate, magnesium stearate, zinc myristate, magnesium myristate, zinc cetyl phosphate, calcium cetyl phosphate, and zinc sodium cetyl phosphate. Further, organic dyes are useful, and examples thereof include tar dyes such as Red #3, Red #104, Red #106, Red #201, Red #202, Red #204, Red #205, Red #220, Red #226, Red #227, Red #228, Red #230, Red #401, Red #505, Yellow #4, Yellow #5, Yellow #202, Yellow #203, Yellow #204, Yellow #401, Blue #1, Blue #2, Blue #201, Blue #404, Green #3, Green #201, Green #204, Green #205, Orange #201, Orange #203, Orange #204, Orange #206, Orange #207, etc. Natural dyes are also useful including carminic acid, laccaic acid, carthamin, brazilin and crocin.

Inorganic/Organic Composite Powder

Exemplary of the inorganic/organic composite powder are composite powders consisting of inorganic particles covered on their surface with organic particles by any well-known method.

It is noted that the powder which has been treated on particle surfaces is also useful. The surface treating agent used therefor is preferably one capable of imparting hydrophobicity in view of the object of not sacrificing the water resistance of products. The surface treating agent is not particularly limited as long as it can impart hydrophobicity. Exemplary are silicone treating agents, waxes, paraffins, organic fluorine compounds of perfluoroalkyl and phosphate salts, surfactants, amino acids such as N-acylglutamic acid, and metal soaps such as aluminum stearate and magnesium myristate. Preferred are silicone treating agents, for example, silicone oils such as caprylsilane (AES-3083 from Shin-Etsu Chemical Co., Ltd.), silanes or silylating agents such as trimethoxysilyldimethicone, dimethyl silicone (KF-96A series from Shin-Etsu Chemical Co., Ltd.), methylhydrogen type polysiloxanes (KF-99P, KF-9901 from Shin-Etsu Chemical Co., Ltd.), silicone-branched silicone treating agents (KF-9908, KF-9909 from Shin-Etsu Chemical Co., Ltd.), and acrylic silicones (KP-574, KP-541 from Shin-Etsu Chemical Co., Ltd.). Furthermore, the foregoing surface hydrophobizing agents may be used alone or in combination of two or more. Examples of the surface treated coloring pigment include KTP-09 series from Shin-Etsu Chemical Co., Ltd., such as KTP-09W, 09R, 09Y, and 09B.

(5) Composition of a Crosslinked Organopolysiloxane (Exclusive of Component (C)) and a Normally Liquid Oil In the composition consisting of a crosslinked organopolysiloxane (exclusive of component (C)) and an oil which is liquid at room temperature, preferably the crosslinked organopolysiloxane is swollen with the liquid oil by taking up the liquid oil in an amount of equal to or more than its own weight. The liquid oil may be cycloalkylmethicone, or a liquid silicone corresponding to component (A), hydrocarbon oil, ester, natural animal or plant oil, semi-synthetic oil or fluorochemical oil may be used. Specific examples of the liquid oil include silicones having a low viscosity of 0.65 to 100 $mm^2/s$ at 25° C., hydrocarbon oils such as liquid paraffin, squalane, isododecane, and isohexadecane, glyceride oils such as trioctanoin, esters such as isotridecyl isononanoate, N-acylglutamic acid esters, and lauroyl sarcosine esters, natural animal or plant oils such as macadamia nut oil and jojoba oil. Unlike component (C), component (5) is a compound having no polyether or polyglycerol structure in its molecular structure, examples of which include KSG series (trade name) from Shin-Etsu Chemical Co., Ltd., such as KSG-15, 16, 016F, 19, 41, 42, 43, 44, 042Z, and 045Z.

(6) Film Forming Agent

The film forming agent is blended mainly for the purpose of maintaining the activity sustainment of products. The agent is preferably selected from silicone base compositions from the standpoint of water repellency, but not limited thereto. For example, trimethylsiloxysilicate, acrylic silicone film forming agents, silicone-modified norbornene, and silicone-modified pullulan may be used. The film forming agent may be dissolved in a normally liquid oil before it is blended in a composition. The liquid oil may be cycloalkylmethicone, or a liquid silicone corresponding to component (A), hydrocarbon oil, ester, natural animal or plant oil, semi-synthetic oil or fluorochemical oil may be used. Specific examples of the liquid oil include silicones having a low viscosity of 0.65 to 100 $mm^2/s$ at 25° C., hydrocarbon oils such as liquid paraffin, squalane, isododecane, and isohexadecane, glyceride oils such as trioctanoin, esters such as isotridecyl isononanoate, N-acylglutamic acid esters, and lauroyl sarcosine esters, natural animal or plant oils such as macadamia nut oil and jojoba oil. Examples include silicone solution of trimethylsiloxysilicate, KF-7312J, silicone solution of acrylic silicone film forming agent, KP-545, KP-549, isododecane solution of silicone-modified norbornene, NBN-30-ID, isododecane solution of silicone-modified pullulan, TSPL-30-ID, dissolved silicone, TSPL-30-D5, all from Shin-Etsu Chemical Co., Ltd.

(7) Other Additives

Other additives include lipophilic gelling agents, UV-absorbing/scattering agents, humectants, preservatives, fragrant agents, salts, antioxidants, pH adjusting agents, chelating agents, refreshing agents, antiinflammatory agents, antifungal agents, skin conditioning agents (e.g., brightening agents, cell activating agents, rough skin improving agents, blood flow promoters, skin astringents, antiseborrheic agents), vitamins, amino acids, nucleic acids, hormones, and inclusions.

Lipophilic Gelling Agent

Suitable lipophilic gelling agents include metal soaps such as aluminum stearate, magnesium stearate, and zinc myristate, amino acid derivatives such as bis-ethylhexyl bis-oleyl pyromellitamide, dibutyl ethylhexanoyl glutamide, dibutyl lauroyl glutamide, N-lauroyl-L-glutamic acid, and α,γ-di-n-butylamine, dextrin fatty acid esters such as dextrin palmitate, dextrin stearate, and dextrin 2-ethylhexanoate palmitate, sucrose fatty acid esters such as sucrose palmitate and sucrose stearate, fructooligosaccharide fatty acid esters such as fructooligosaccharide stearate and fructooligosaccharide 2-ethylhexanoate, benzylidene derivatives of sorbitol such as monobenzylidene sorbitol and dibenzylidene sorbitol, and organic modified clay minerals such as dimethyl benzyl dodecyl ammonium montmorillonite clay, dimethyl dioctadecyl ammonium montmorillonite clay, and dimethyl dioctadecyl ammonium hectolite clay.

UV Absorbing/Scattering Agent

Suitable UV absorbing/scattering agents include UV absorbing/scattering particles such as microparticulate titanium oxide, microparticulate iron-containing titanium oxide, microparticulate zinc oxide, microparticulate cerium oxide, and composites thereof. A dispersion obtained by previously dispersing UV absorbing/scattering particles in an oil is also useful. The oil used herein may be cycloalkylmethicone, or a liquid silicone corresponding to component (A), hydrocarbon oil, ester, natural animal or plant oil, semi-synthetic oil or fluorochemical oil may be used. Specific examples of the oil include silicones having a low viscosity of 0.65 to 100 $mm^2/s$ at 25° C., hydrocarbon oils such as liquid paraffin, squalane, isododecane, and isohexadecane, glyceride oils such as trioctanoin, esters such as isotridecyl isononanoate, N-acylglutamic acid esters, and lauroyl sarcosine esters, natural animal or plant oils such as macadamia nut oil. Examples of the dispersion of UV absorbing/scattering particles in oil include SPD series (trade name) from Shin-Etsu Chemical Co., Ltd., such as SPD-T5, Z5, T6, and Z6.

Humectant

Suitable humectants include polyethylene glycol, hyaluronic acid, chondroitin sulfate, pyrrolidone carboxylate, polyoxyethylene methyl glucoside, polyoxypropylene methyl glucoside, egg yolk lecithin, soy lecithin, phosphatidylcholine, phosphatidyl ethanol amine, phosphatidyl serine, phosphatidyl glycerol, phosphatidyl inositol, and sphingophospholipid as well as alcoholic hydroxyl group-containing compounds other than components (2) and (A), in an overlapping manner.

Preservative

Preservatives are compounds exclusive of the bactericide (B) and blended for the purpose of preventing the product from bacterial contamination. Suitable preservatives include alkyl p-hydroxybenzoates, benzoic acid, sodium benzoate, sorbic acid, potassium sorbate, and phenoxyethanol.

Suitable antifungal agents include benzoic acid, carbolic acid, sorbic acid, alkyl p-hydroxybenzoates, p-chloro-m-cresol, hexachlorophene, trichlorocarbaniride, photosensitizer, and phenoxyethanol.

Fragrant Agent

Fragrant agents include naturally occurring fragrant agents and synthetic fragrant agents. Suitable natural fragrant agents include plant fragrant agents extracted from flowers, leaves, trunks and skins, and animal fragrant agents such as musk and civet. Suitable synthetic fragrant agents include hydrocarbons such as monoterpene, alcohols such as aliphatic alcohols and aromatic alcohols, aldehydes such as terpene aldehydes and aromatic aldehydes, ketones such as alicyclic ketones, esters such as terpene base esters, lactones, phenols, oxides, nitrogen-containing compounds, and acetals.

Salt

Salts are compounds exclusive of the antiperspirant (B). Suitable salts include inorganic salts, organic acid salts, amine salts, and amino acid salts. Exemplary inorganic salts include sodium, potassium, magnesium, calcium, aluminum, zirconium and zinc salts of inorganic acids such as hydrochloric acid, sulfuric acid, carbonic acid, and nitric acid. Exemplary organic acid salts include salts of organic acids such as acetic acid, dehydroacetic acid, citric acid, malic acid, succinic acid, ascorbic acid, and stearic acid. Exemplary amine salts and amino acid salts include salts of amines such as triethanolamine, and salts of amino acids such as glutamic acid. In addition, hyaluronic acid, chondroitin sulfate and similar salts, and neutralized salts of acid-alkali as used in preparation formulations may be used.

Antioxidant

Suitable antioxidants include, but are not limited to, carotenoid, ascorbic acid and salts thereof, ascorbyl stearate, tocophenol, tocophenol acetate, tocopherol, p-t-butylphenol, butylhydroxyanisole, dibutylhydroxytoluene, phytic acid, ferulic acid, thiotaurine, hypotaurine, sulfites, erythorbic acid and salts thereof, chlorogenic acid, epicatechin, epigallocatechin, epigallocatechin gallate, apigenin, kaempferol, myricetin, and quercetin.

pH Adjusting Agent

Suitable pH adjusting agents include lactic acid, citric acid, glycolic acid, succinic acid, tartaric acid, dl-malic acid, potassium carbonate, sodium hydrogencarbonate, and ammonium hydrogencarbonate.

Chelating Agent

Suitable chelating agents include alanine, sodium salt of EDTA, sodium polyphosphate, sodium metaphosphate, and phosphoric acid.

Refreshing Agent

Suitable refreshing agents include L-menthol, camphor, and menthyl lactate.

Antiinflammatory Agent

Suitable antiinflammatory agents include arantoin, glycyrrhizic acid and salts thereof, glycyrrhetinic acid, stearyl glycyrrhetinate, tranexamic acid, and azulene.

Skin Improving Agent

Suitable skin improving agents include brightening agents such as placenta extract, arbutin, glutathione and Saxifrage stolonifera extract; cell activating agents such as royal jelly, photosensitizer, cholesterol derivatives, bovine blood extract; anti-skin-roughening agents; blood flow promotors such as nonanoic acid vanillylamide, benzyl nicotinate,β-butoxyethyl nicotinate, capsaicin, zingerone, cantharides tincture, ichthammol, caffeine, tannic acid, a-borneol, nicotinic acid tocopherol, inositol hexanicotinate, cyclandelate, cinnarizine, tolazoline, acetylcholine, verapamil, cepharanthine, and y-oryzanol; skin astringents; antiseborrheic agents such as sulfur and thianthrol.

Vitamin

Suitable vitamins include vitamin A species such as vitamin A oil, retinol, retinol acetate, and retinol palmitate; vitamin B species, for example, vitamin B2 species such as riboflavin, riboflavin butyrate, and flavin adenine nucleotide, vitamin B6 species such as pyridoxine hydrochloride, pyridoxine dioctanoate, and pyridoxine tripalmitate, vitamin B12 and derivatives thereof, vitamin B15 and derivatives thereof; vitamin C species such as L-ascorbic acid, L-ascorbic acid dipalmitic acid ester, sodium L-ascorbic acid-2-sulfate, and dipotassium L-ascorbic acid phosphoric acid diester; vitamin D species such as ergocalciferol and cholecalciferol; vitamin E species such as α-tocopherol, β-tocopherol, γ-tocopherol, dl-α-tocopherol acetate, dl-α-tocopherol nicotinate, and dl-α-tocopherol succinate; nicotinic acids such as nicotinic acid, benzyl nicotinate and nicotinic acid amide; vitamin H; vitamin P; pantothenic acids such as calcium pantothenate, D-pantothenyl alcohol, pantothenyl ethyl ether, and acetylpantothenyl ethyl ether, and biotin.

Amino Acid

Suitable amino acids include glycine, valine, leucine, isoleucine, serine, threonine, phenylalanine, arginine, lysine, aspartic acid, glutamic acid, cystine, cysteine, methionine, and tryptophan.

Nucleic Acid

Typical of the nucleic acid is deoxyribonucleic acid.

Hormone

Suitable hormones include estradiol and ethenylestradiol.

Inclusion Compound

Typical of the inclusion compound is cyclodextrin.

[Preparation Method]

The method for preparing the water-in-oil emulsion type stick-shaped deodorant composition of the invention is not particularly limited. For example, a water-in-oil emulsion may be obtained by mixing oil phase components and heating the mixture at 70 to 110° C., separately mixing water phase components and heating the mixture at 70 to 90° C., then adding the water phase to the oil phase. The emulsion is filled into a stick container and cooled, yielding a stick-shaped deodorant composition.

[Water-in-Oil Emulsion Type Stick-Shaped Deodorant Composition]

The water-in-oil emulsion type stick-shaped deodorant composition of the invention is not particularly limited as long as it is of water-in-oil emulsion type. Also, it is not particularly limited in size or the like as long as it is of stick shape.

EXAMPLES

Examples and Comparative Examples are given below for further illustrating the invention although the invention is not limited thereto. While the embodiments are merely exemplary, any embodiments having substantially the same construction as the technical concept set forth in the following claims and exerting equivalent functions and results are believed to be within the spirit and scope of the invention. Herein, % in formulation is by weight unless otherwise stated.

EXAMPLES AND COMPARATIVE EXAMPLES

Water-in-oil emulsion type stick-shaped deodorant compositions of the formulation shown in Tables 2 and 3 were prepared by the following method and evaluated for various properties. The results are also shown in Tables 2 and 3.

<Preparation of Deodorant Composition>

A stick-shaped deodorant composition was prepared by the steps:

A: intimately mixing component (1) and heating at 95° C.,

B: intimately mixing component (2) and heating at 85° C., and

C: adding B to A, emulsifying, filling into a stick container of diameter 18 mm, and cooling.

(1) Evaluation of Properties

A panel of 10 panelists evaluated the water-in-oil emulsion type stick-shaped deodorant compositions with respect to feeling on use (non-stickiness), extensibility (easy spread), dry feeling (whether a dry feeling is adequate or excessive), water resistance (retention against perspiration), and stick's collapse resistance (portability). Ratings were assigned according to the criteria shown in Table 3. An average was calculated from ratings of 10 panelists and judged according to the following judgment criteria.

TABLE 1

| | Feeling on use | Extensibility | Dry feeling | Water resistance | Stick collapse resistance |
|---|---|---|---|---|---|
| 5 | non-sticky | exc. | exc. | perspiration resistant | collapse resistant |
| 4 | less sticky | good | good | somewhat perspiration resistant | somewhat collapse resistant |
| 3 | mediocre | mediocre | mediocre | mediocre | mediocre |
| 2 | somewhat sticky | rather poor | rather excessive or less perceivable | some removal with perspiration | somewhat collapsible |
| 1 | sticky | poor | excessive or non-perceivable | removal with perspiration | collapsible |

(2) Judgment criteria

⊙: average point 4.5

○: 3.5≤average point<4.5

Δ: 2.5≤average point<3.5

X: 1.5≤average point<2.5

XX: average point<1.5

A sample rated Δ or better is judged "pass."

(3) Stick's Resistance to Thinning

A stick-shaped deodorant composition was stored in a thermostat tank at 25° C. for 1 month before its shape was observed with naked eyes. The stick was rated "⊙" when it was unchanged or substantially unthinned from immediately after filling, "Δ" when it was somewhat thinned, and "×" when it was apparently thinned.

(4) Stability

A stick-shaped deodorant composition was stored in a thermostat tank at 50° C. for 1 month before its shape was observed with naked eyes and its feeling was examined by applying to the skin. The stick was rated "×" when problems like separation and feeling changes were found, and "⊙" for no problems.

TABLE 2

| | Formulation (%) | Example | | | | | | | | |
|---|---|---|---|---|---|---|---|---|---|---|
| | | 1 | 2 | 3 | 4 | 5 | 6 | 7 | 8 | 9 |
| (1) | (C) Partially crosslinked polyether-modified silicone composition*[1] | 5 | 5 | 5 | 5 | 5 | 5 | 5 | 5 | 5 |
| | (D) Silicone-branched polyether-modified silicone*[2] | 1 | 1 | 1 | 1 | 1 | 1 | 1 | 1 | 1 |

TABLE 2-continued

|  | Formulation (%) | Example | | | | | | | | |
| --- | --- | --- | --- | --- | --- | --- | --- | --- | --- | --- |
|  |  | 1 | 2 | 3 | 4 | 5 | 6 | 7 | 8 | 9 |
|  | Dimethylpolysiloxane (6cs) | 10 | 5 | 5 | 5 | 5 |  | 10 |  | 24 |
|  | Diphenylsiloxyphenyltrimethicone*3 | 9.7 | 9.7 | 9.7 | 9.7 | 9.7 | 9.7 | 9.7 | 10 | 20.7 |
|  | (A) Cyclopentasiloxane |  | 5 |  |  |  | 5 |  | 11.7 |  |
|  | (A) Dimethylpolysiloxane (2cs) |  |  | 5 |  |  |  |  |  |  |
|  | (A) Tristrimethylsiloxymethylsilane*4 |  |  |  | 10 |  |  |  |  |  |
|  | (A) Isododecane |  |  |  |  | 5 | 5 |  |  |  |
|  | (E) Ceresin | 7 | 7 | 7 | 7 | 7 | 7 | 7 | 7 | 12 |
|  | (B) Aluminum hydrochloride | 1 | 1 | 1 | 1 | 1 | 1 | 1 | 1 | 1 |
|  | (B) Isopropylmethylphenol | 0.1 | 0.1 | 0.1 | 0.1 | 0.1 | 0.1 | 0.1 | 0.1 | 0.1 |
| (2) | Butylene glycol (BG) | 5 | 5 | 5 | 5 | 5 | 5 | 15 | 5 | 5 |
|  | Sodium chloride | 1 | 1 | 1 | 1 | 1 | 1 | 1 | 1 | 1 |
|  | Sodium citrate | 0.2 | 0.2 | 0.2 | 0.2 | 0.2 | 0.2 | 0.2 | 0.2 | 0.2 |
|  | (A) Ethanol | 10 | 10 | 10 | 10 | 10 | 10 |  | 10 | 10 |
|  | (A) Purified water | 50 | 50 | 50 | 50 | 50 | 50 | 50 | 48 | 20 |
| Total |  | 100.0 | 100.0 | 100.0 | 100.0 | 100.0 | 100.0 | 100.0 | 100.0 | 100.0 |
|  | Total of component (A) | 60 | 65 | 65 | 65 | 65 | 70 | 50 | 69.7 | 30 |
|  | Proportion (%) of water and ethanol in component (A) | 100 | 92 | 92 | 92 | 92 | 86 | 100 | 83 | 100 |
| Evaluation | Feeling on use | ◎ | ◎ | ◎ | ◎ | ◎ | ◎ | ○ | ◎ | ○ |
|  | Extensibility | ◎ | ◎ | ◎ | ○ | ○ | ○ | ◎ | ○ | ○ |
|  | Dry feeling | ◎ | ○ | ○ | ○ | ○ | Δ | ◎ | Δ | Δ |
|  | Water resistance | ◎ | ◎ | ◎ | ◎ | ◎ | ○ | ○ | ○ | ◎ |
|  | Stick collapse resistance | ◎ | ◎ | ◎ | ◎ | ◎ | ◎ | ◎ | ○ | ○ |
|  | Stick thinning resistance | ◎ | ◎ | ◎ | ◎ | ◎ | Δ | ◎ | Δ | ◎ |
|  | Stability | ◎ | ◎ | ◎ | ◎ | ◎ | ◎ | ◎ | ◎ | ◎ |

TABLE 3

|  | Formulation (%) | Comparative Example | | | | | | | |
| --- | --- | --- | --- | --- | --- | --- | --- | --- | --- |
|  |  | 1 | 2 | 3 | 4 | 5 | 6 | 7 | 8 |
| (1) | (C) Partially crosslinked polyether-modified silicone composition*1 |  | 5 | 5 | 5 | 5 | 5 | 5 | 5 |
|  | (D) Silicone-branched polyether-modified silicone*2 | 1 |  | 1 | 1 | 1 | 1 | 1 | 1 |
|  | Dimethylpolysiloxane (6cs) | 15 | 11 |  |  |  |  |  |  |
|  | Diphenylsiloxyphenyltrimethicone*3 | 9.7 | 9.7 | 6.7 | 6.7 | 6.7 | 6.7 | 6.7 | 6.7 |
|  | (A) Cyclopentasiloxane |  |  | 13 | 13 | 15 |  |  |  |
|  | (A) Dimethylpolysiloxane (2cs) |  |  |  |  |  | 15 |  |  |
|  | (A) Tristrimethylsiloxymethylsilane*4 |  |  |  |  |  |  | 15 |  |
|  | (A) Isododecane |  |  |  |  |  |  |  | 15 |
|  | (E) Ceresin | 7 | 7 | 7 | 7 | 7 | 7 | 7 | 7 |
|  | (B) Aluminum hydrochloride | 1 | 1 | 1 | 1 | 1 | 1 | 1 | 1 |
|  | (B) Isopropylmethylphenol | 0.1 | 0.1 | 0.1 | 0.1 | 0.1 | 0.1 | 0.1 | 0.1 |
| (2) | Butylene glycol (BG) | 5 | 5 | 14 | 5 | 5 | 5 | 5 | 5 |
|  | Sodium chloride | 1 | 1 | 1 | 1 | 1 | 1 | 1 | 1 |
|  | Sodium citrate | 0.2 | 0.2 | 0.2 | 0.2 | 0.2 | 0.2 | 0.2 | 0.2 |
|  | (A) Ethanol | 10 | 10 | 10 | 10 | 10 | 10 | 10 | 10 |
|  | (A) Purified water | 50 | 50 | 41 | 54 | 48 | 48 | 48 | 48 |
| Total |  | 100.0 | 100.0 | 100.0 | 100.0 | 100.0 | 100.0 | 100.0 | 100.0 |
|  | Total of component (A) | 60 | 60 | 64 | 77 | 73 | 73 | 73 | 73 |
|  | Proportion (%) of water and ethanol in component (A) | 100 | 100 | 80 | 83 | 79 | 79 | 79 | 79 |
| Evaluation | Feeling on use | X | ◎ | ◎ | ◎ | ◎ | ◎ | ◎ | ◎ |
|  | Extensibility | ○ | ◎ | Δ | Δ | X | X | X | X |
|  | Dry feeling | ◎ | ◎ | X | X | XX | XX | XX | XX |
|  | Water resistance | ◎ | ◎ | Δ | Δ | X | X | X | X |
|  | Stick collapse resistance | X | XX | ○ | ○ | ○ | ○ | ○ | ○ |
|  | Stick thinning resistance | ◎ | ◎ | X | X | X | X | X | X |
|  | Stability | X | X | ◎ | ◎ | ◎ | ◎ | ◎ | ◎ |

TABLE 4

|  | Formulation (%) | Comparative Example 9 | Comparative Example 10 | Comparative Example 11 |
|---|---|---|---|---|
| (1) | (C) Partially crosslinked polyether-modified silicone composition*1 | 5 | 5 | 5 |
|  | (D) Silicone-branched polyether-modified silicone*2 | 1 | 1 | 1 |
|  | Dimethylpolysiloxane (6cs) | 39 | 10 | 17 |
|  | Diphenylsiloxyphenyltrimethicone*3 | 10.7 | 9.7 | 9.7 |
|  | (E) Ceresin | 12 | 7 |  |
|  | (B) Aluminum hydrochloride | 1 | 1 | 1 |
|  | (B) Isopropylmethylphenol | 0.1 | 0.1 | 0.1 |
| (2) | Butylene glycol (BG) | 5 | 40 | 5 |
|  | Sodium chloride | 1 | 1 | 1 |
|  | Sodium citrate | 0.2 | 0.2 | 0.2 |
|  | (A) Ethanol | 10 | 10 | 10 |
|  | (A) Purified water | 15 | 15 | 50 |
|  | Total | 100.0 | 100.0 | 100.0 |
|  | Total of component (A) | 25 | 25 | 60 |
|  | Proportion (%) of water and ethanol in component (A) | 100 | 100 | 100 |
| Evaluation | Feeling on use | ○ | X | X |
|  | Extensibility | ○ | ○ | Δ |
|  | Dry feeling | X | X | ◎ |
|  | Water resistance | ◎ | Δ | ◎ |
|  | Stick collapse resistance | X | Δ | — |
|  | Stick thinning resistance | ◎ | ◎ | — |
|  | Stability | X | X | X |

*1 Partially crosslinked polyether-modified silicone composition: KSG-210 (crosslinked part ~25%, dimethylpolysiloxane (6 cs) ~75%) from Shin-Etsu Chemical Co., Ltd.
*2 Silicone-branched polyether-modified silicone composition: KF-6028 from Shin-Etsu Chemical Co., Ltd.
*3 Diphenyl siloxyphenyltrimethicone: KF-56A from Shin-Etsu Chemical Co., Ltd.
*4 Tristrimethylsiloxymethylsilane: TMF-1.5 from Shin-Etsu Chemical Co., Ltd.

When a composition is used, the blended amount is the amount of the composition (the same holds true, hereinafter).

It was demonstrated that the water-in-oil emulsion type stick-shaped deodorant compositions of Examples 1 to 9 were satisfactory with respect to feeling on use (non-stickiness), extensibility (easy spread), dry feeling (whether a dry feeling is adequate or excessive), water resistance (retention against perspiration), stick's collapse resistance (portability), stick's thinning resistance, and product stability (50° C./1 month).

In contrast, the compositions of Comparative Examples 1 and 2 not using component (C) or (D) lacked stability because of poor emulsion state. The compositions of Comparative Examples 3 to 10 wherein the total of component (A) was outside the range of 30 to 70% by weight, or the proportion of the sum of water and ethanol in component (A) was less than 83% by weight failed to meet satisfactory properties. The composition of Comparative Example 11 not using component (E) could not be shaped into a stick.

Example 10

Stick-Shaped Deodorant Composition
<Preparation>

A stick-shaped deodorant composition was prepared by step A of mixing ingredients 1 to 8 until uniform and heating at 95° C., step B of mixing ingredients 9 to 15 until uniform and heating at 85° C., and step C of adding B to A, emulsifying, adding ingredient 16, uniformly mixing, filling the emulsion into a stick container, and cooling.

| Formulation | % |
|---|---|
| 1. Alkyl-modified, partially crosslinked polyether-modified silicone composition*1 | 3.5 |
| 2. Silicone/alkyl-branched, polyether-modified silicone*2 | 0.5 |
| 3. Alkyl-modified, partially crosslinked dimethylpolysiloxane composition*3 | 3 |
| 4. Triethylhexanoin | 5 |
| 5. Tristrimethylsiloxymethylsilane*4 | 5 |
| 6. Stearyl alcohol | 8 |
| 7. Paraffin | 2 |
| 8. Dibutylhydroxytoluene | 0.02 |
| 9. Aluminum hydrochloride | 23 |
| 10. Dipropylene glycol | 3 |
| 11. Ethanol | 20 |
| 12. Phenoxyethanol | 0.3 |
| 13. Sodium citrate | 0.2 |
| 14. Sodium chloride | 1 |
| 15. Purified water | balance |
| 16. Fragrance | adequate |
| Total | 100.0 |

Total of component (A): 50%
Proportion of the sum of water and ethanol in component (A): 90%

*1 Alkyl-modified (branched), partially crosslinked polyether-modified silicone composition: KSG-330 (crosslinked part ~20%, triethylhexanoin ~80%) from Shin-Etsu Chemical Co., Ltd.
*2 Silicone/alkyl-branched, polyether-modified silicone: KF-6038 from Shin-Etsu Chemical Co., Ltd.
*3 Alkyl-modified (branched), partially crosslinked dimethylpolysiloxane composition: KSG-43 (crosslinked part ~30%, triethylhexanoin ~70%) from Shin-Etsu Chemical Co., Ltd.
*4 Tristrimethylsiloxymethylsilane: TMF-1.5 from Shin-Etsu Chemical Co., Ltd.

The resulting stick-shaped deodorant composition was found to have satisfactory feeling on use, extendability, dry feeling, perspiration resistance, and portability as well as storage stability.

Example 11

Stick-Shaped Deodorant Composition
<Preparation>

A stick-shaped deodorant composition was prepared by step A of mixing ingredients 1 to 12 until uniform and heating at 95° C., step B of mixing ingredients 13 to 20 until uniform and heating at 85° C., and step C of adding B to A, emulsifying, filling the emulsion into a stick container, and cooling.

| | Formulation | % |
|---|---|---|
| 1. | Alkyl-modified, partially crosslinked polyglycerol-modified silicone composition*[1] | 3.5 |
| 2. | Silicone/alkyl-branched, polyglycerol-modified silicone*[2] | 1.5 |
| 3. | Partially crosslinked dimethylpolysiloxane composition*[3] | 3 |
| 4. | Dimethylpolysiloxane (6cs) | 2 |
| 5. | Diphenylsiloxyphenyltrimethicone*[4] | 7 |
| 6. | Tristrimethylsiloxymethylsilane*[5] | 5 |
| 7. | Trimethylsiloxysilicate solution*[6] | 2 |
| 8. | Inulin stearate*[7] | 0.5 |
| 9. | Polyethylene | 6 |
| 10. | Microcrystalline wax | 1.5 |
| 11. | Dibutylhydroxytoluene | 0.02 |
| 12. | Aluminum zirconium trichlorohydrex gly | 15.5 |
| 13. | Benzalkonium chloride | 0.05 |
| 14. | Glycerol | 3 |
| 15. | Ethanol | 40 |
| 16. | Phenoxyethanol | 0.3 |
| 17. | Sodium citrate | 0.2 |
| 18. | Sodium chloride | 1 |
| 19. | Purified water | balance |
| 20. | Menthol | 0.03 |
| | Total | 100.0 |

Total of component (A): 57%
Proportion of the sum of water and ethanol in component (A): 84%

*[1]Alkyl-modified (branched), partially crosslinked polyglycerol-modified silicone composition: KSG-830 (crosslinked part ~20%, triethylhexanoin ~80%) from Shin-Etsu Chemical Co., Ltd.
*[2]Silicone/alkyl-branched, polyglycerol-modified silicone: KF-6105 from Shin-Etsu Chemical Co., Ltd.
*[3]Partially crosslinked dimethylpolysiloxane composition: KSG-15 (crosslinked part ~7%, cyclopentasiloxane ~93%) from Shin-Etsu Chemical Co., Ltd.
*[4]Diphenylsiloxyphenyltrimethicone: KF-56A from Shin-Etsu Chemical Co., Ltd.
*[5]Tristrimethylsiloxymethylsilane: TMF-1.5 from Shin-Etsu Chemical Co., Ltd.
*[6]Trimethylsiloxysilicate solution: KF-7312J (solids ~50%, cyclopentasiloxane ~50%) from Shin-Etsu Chemical Co., Ltd.
*[7]Inulin stearate: Rheopearl ISK2 by Chiba Flour Milling Co., Ltd.

The resulting stick-shaped deodorant composition was found to have satisfactory feeling on use, perspiration resistance, and portability as well as storage stability.

Example 12

Stick-Shaped Deodorant Composition
<Preparation>

A stick-shaped deodorant composition was prepared by step A of mixing ingredients 1 to 9 until uniform and heating at 95° C., step B of mixing ingredients 10 to 16 until uniform and heating at 85° C., and step C of adding B to A, emulsifying, adding ingredient 17, uniformly mixing, filling the emulsion into a stick container, and cooling.

| | Formulation | % |
|---|---|---|
| 1. | Silicone/alkyl-branched, partially crosslinked polyether-modified silicone composition*[1] | 3.5 |
| 2. | Polyether-modified silicone*[2] | 0.5 |
| 3. | Partially crosslinked dimethylpolysiloxane composition*[3] | 3 |
| 4. | Dimethylpolysiloxane (6cs) | 3 |
| 5. | Diphenylsiloxyphenyltrimethicone*[4] | 5 |
| 6. | Isotridecyl isononanoate | 5 |
| 7. | Dextrin palmitate/ethylhexanoate*[5] | 2 |
| 8. | Ceresin | 7 |
| 9. | Zinc p-phenol sulfonate | 2 |
| 10. | Sodium hyaluronate (2% solution) | 5 |
| 11. | Glycerol | 3 |
| 12. | Butylene glycol | 8 |
| 13. | Ethylhexylglycerol | 0.05 |
| 14. | Sodium citrate | 0.2 |
| 15. | Sodium chloride | 1 |
| 16. | Purified water | balance |
| 17. | Fragrance | adequate |
| | Total | 100.0 |

Total of component (A): 57%
Proportion of the sum of water and ethanol in component (A): 100%

*[1]Silicone/alkyl-branched, partially crosslinked polyether-modified silicone composition: KSG-360Z (crosslinked part ~35%, dimethicone (6cs) ~65%) from Shin-Etsu Chemical Co., Ltd.
*[2]Polyether-modified silicone: KF-6017 from Shin-Etsu Chemical Co., Ltd.
*[3]Partially crosslinked dimethylpolysiloxane composition: KSG-016F (crosslinked part ~25%, dimethicone (6cs) ~75%) from Shin-Etsu Chemical Co., Ltd.
*[4]Diphenylsiloxyphenyltrimethicone: KF-56A from Shin-Etsu Chemical Co., Ltd.
*[5]Dextrin palmitate/ethylhexanoate: Rheopearl TT2 by Chiba Flour Milling Co., Ltd.

The resulting stick-shaped deodorant composition was found to have satisfactory feeling on use, extensibility, dry feeling, perspiration resistance, and portability as well as storage stability.

Example 13

Stick-Shaped Deodorant Composition
<Preparation>

A stick-shaped deodorant composition was prepared by step A of mixing ingredients 1 to 9 until uniform and heating at 95° C., step B of mixing ingredients 10 to 16 until uniform and heating at 85° C., and step C of adding B to A, emulsifying, filling the emulsion into a stick container, and cooling.

| | Formulation | % |
|---|---|---|
| 1. | Silicone/alkyl-branched, partially crosslinked polyglycerol-modified silicone composition*[1] | 3.5 |
| 2. | Silicone/alkyl-branched, polyglycerol-modified silicone*[2] | 1.5 |
| 3. | Silicone/alkyl-branched, partially crosslinked dimethylpolysiloxane composition*[3] | 3 |
| 4. | Acrylic-silicone film former solution*[4] | 3 |
| 5. | Neopentylglycol diethylhexanoate | 8 |
| 6. | Isononyl isononanoate | 2 |
| 7. | Dextrin palmitate*[5] | 2 |
| 8. | Synthetic wax | 7 |
| 9. | Triclosan | 0.1 |
| 10. | Dipropylene glycol | 5 |
| 11. | Glycerol | 3 |
| 12. | Butylene glycol | 8 |
| 13. | Methyl paraben | 0.15 |
| 14. | Sodium citrate | 0.2 |
| 15. | Sodium chloride | 1 |
| 16. | Purified water | balance |
| | Total | 100.0 |

Total of component (A): 58%
Proportion of the sum of water and ethanol in component (A): 91%

*[1]Silicone/alkyl-branched, partially crosslinked polyglycerol-modified silicone composition: KSG-850Z (crosslinked part ~25%, cyclopentasiloxane ~75%) from Shin-Etsu Chemical Co., Ltd.
*[2]Silicone/alkyl-branched, polyglycerol-modified silicone: KF-6105 from Shin-Etsu Chemical Co., Ltd.
*[3]Silicone/alkyl-branched, partially crosslinked dimethylpolysiloxane composition: KSG-042Z (crosslinked part ~20%, isododecane ~80%) from Shin-Etsu Chemical Co., Ltd.
*[4]Acrylic-silicone film former solution: KP-550 (solids 40%, isododecane 60%) from Shin-Etsu Chemical Co., Ltd.
*[5]Dextrin palmitate: Rheopearl KL2 by Chiba Flour Milling Co., Ltd.

The resulting stick-shaped deodorant composition was found to have satisfactory feeling on use, extensibility, dry feeling, perspiration resistance, and portability as well as storage stability.

Example 14

Stick-Shaped Deodorant Composition
<Preparation>

A stick-shaped deodorant composition was prepared by step A of mixing ingredients 1 to 10 until uniform and heating at 95° C., step B of mixing ingredients 11 to 17 until uniform and heating at 85° C., and step C of adding B to A, emulsifying, filling the emulsion into a stick container, and cooling.

| | Formulation | % |
|---|---|---|
| 1. | Partially crosslinked polyether-modified silicone composition*¹ | 3.5 |
| 2. | Polyether-modified silicone*² | 1.2 |
| 3. | Phenyl-modified, partially crosslinked dimethylpolysiloxane composition*³ | 3 |
| 4. | Dimethylpolysiloxane (6cs) | 3 |
| 5. | Diphenylsiloxyphenyltrimethicone*⁴ | 5 |
| 6. | Ethylhexyl palmitate | 4 |
| 7. | Silicone wax*⁵ | 2 |
| 8. | Ceresin | 7 |
| 9. | Alkyl-modified silicone composite powder*⁶ | 1 |
| 10. | Dry aluminum potassium sulfate | 2 |
| 11. | Allantoin | 0.2 |
| 12. | Pentylene glycol | 2 |
| 13. | Butylene glycol | 8 |
| 14. | Phenoxyethanol | 0.2 |
| 15. | Sodium citrate | 0.2 |
| 16. | Sodium chloride | 1 |
| 17. | Purified water | balance |
| | Total | 100.0 |

Total of component (A): 57%
Proportion of the sum of water and ethanol in component (A): 100%

*¹Partially crosslinked polyether-modified silicone composition: KSG-210 (crosslinked part ~25%, dimethicone (6cs) ~75%) from Shin-Etsu Chemical Co., Ltd.
*²Polyether-modified silicone: KF-6017 from Shin-Etsu Chemical Co., Ltd.
*³Phenyl-modified, partially crosslinked dimethylpolysiloxane composition: KSG-18A (crosslinked part ~15%, diphenylsiloxyphenyltrimethicone ~85%) from Shin-Etsu Chemical Co., Ltd.
*⁴Diphenylsiloxyphenyltrimethicone: KF-56A from Shin-Etsu Chemical Co., Ltd.
*⁵Silicone wax: KP-561P from Shin-Etsu Chemical Co., Ltd.
*⁶Alkyl-modified silicone composite powder: KSP-441 from Shin-Etsu Chemical Co., Ltd.

The resulting stick-shaped deodorant composition was found to have satisfactory feeling on use, extensibility, dry feeling, perspiration resistance, and portability as well as storage stability.

Example 15

Stick-Shaped Deodorant Composition
<Preparation>

A stick-shaped deodorant composition was prepared by step A of mixing ingredients 1 to 10 until uniform and heating at 95° C., step B of mixing ingredients 11 to 17 until uniform and heating at 85° C., and step C of adding B to A, emulsifying, filling the emulsion into a stick container, and cooling.

| | Formulation | % |
|---|---|---|
| 1. | Partially crosslinked polyglycerol-modified silicone composition*¹ | 4 |
| 2. | Silicone-branched, polyglycerol-modified silicone*² | 1.4 |
| 3. | Phenyl-modified, partially crosslinked dimethylpolysiloxane composition*³ | 3 |
| 4. | Diphenylsiloxyphenyltrimethicone*⁴ | 8 |
| 5. | Isotridecyl isononanoate | 5 |
| 6. | Silicone wax*⁵ | 1 |
| 7. | Candelilla wax | 6 |
| 8. | Carnauba wax | 2 |
| 9. | Silicone composite powder*⁶ | 5 |
| 10. | Isopropylmethylphenol | 0.1 |
| 11. | γ-Glycyrrhizinic acid | 0.2 |
| 12. | Pentylene glycol | 2 |
| 13. | Dipropylene glycol | 8 |
| 14. | Phenoxyethanol | 0.2 |
| 15. | Sodium citrate | 0.2 |
| 16. | Sodium chloride | 1 |
| 17. | Purified water | balance |
| | Total | 100.0 |

Total of component (A): 53%
Proportion of the sum of water and ethanol in component (A): 100%

*¹Partially crosslinked polyglycerol-modified silicone composition: KSG-710 (crosslinked part ~25%, dimethicone (6cs) ~75%) from Shin-Etsu Chemical Co., Ltd.
*²Silicone-branched, polyglycerol-modified silicone: KF-6104 from Shin-Etsu Chemical Co., Ltd.
*³Phenyl-modified, partially crosslinked dimethylpolysiloxane composition: KSG-18A (crosslinked part ~15%, diphenylsiloxyphenyltrimethicone ~85%) from Shin-Etsu Chemical Co., Ltd.
*⁴Diphenylsiloxyphenyltrimethicone: KF-56A from Shin-Etsu Chemical Co., Ltd.
*⁵Silicone wax: KP-562P from Shin-Etsu Chemical Co., Ltd.
*⁶Silicone composite powder: KSP-105 from Shin-Etsu Chemical Co., Ltd.

The resulting stick-shaped deodorant composition was found to have satisfactory feeling on use, extensibility, dry feeling, perspiration resistance, and portability as well as storage stability.

Example 16

Stick-Shaped Deodorant Composition
<Preparation>

A stick-shaped deodorant composition was prepared by step A of mixing ingredients 1 to 10 until uniform and heating at 95° C., step B of mixing ingredients 11 to 17 until uniform and heating at 85° C., and step C of adding B to A, emulsifying, adding ingredient 18, uniformly mixing, filling the emulsion into a stick container, and cooling.

| | Formulation | % |
|---|---|---|
| 1. | Partially crosslinked polyether-modified silicone composition*¹ | 3 |
| 2. | Silicone/alkyl-branched, polyether-modified silicone*² | 1 |
| 3. | Partially crosslinked dimethylpolysiloxane composition*³ | 1 |
| 4. | Dimethylpolysiloxane (6cs) | 6 |
| 5. | Diphenylsiloxyphenyltrimethicone*⁴ | 6 |
| 6. | Microcrystalline wax | 2 |
| 7. | Synthetic wax | 2 |
| 8. | Ceresin | 7 |
| 9. | Stearyl glycyrrhizinate | 0.2 |
| 10. | Aluminum hydrochloride | 3 |
| 11. | Benzalkonium chloride | 0.05 |
| 12. | Pentylene glycol | 3 |
| 13. | Butylene glycol | 8 |
| 14. | Tea extract | 0.2 |
| 15. | Sodium citrate | 0.2 |

-continued

| Formulation | % |
|---|---|
| 16. Sodium chloride | 1 |
| 17. Purified water | balance |
| 18. Fragrance | adequate |
| Total | 100.0 |

Total of component (A): 56%
Proportion of the sum of water and ethanol in component (A): 100%

*[1] Partially crosslinked polyether-modified silicone composition: KSG-210 (crosslinked part ~25%, dimethicone (6cs) ~75%) from Shin-Etsu Chemical Co., Ltd.
*[2] Silicone/alkyl-branched, polyether-modified silicone: KF-6038 from Shin-Etsu Chemical Co., Ltd.
*[3] Partially crosslinked dimethylpolysiloxane composition: KSG-19 (crosslinked part ~15%, dimethicone (6cs) ~85%) from Shin-Etsu Chemical Co., Ltd.
*[4] Diphenylsiloxyphenyltrimethicone: KF-56A from Shin-Etsu Chemical Co., Ltd.

The resulting stick-shaped deodorant composition was found to have satisfactory feeling on use, extensibility, dry feeling, perspiration resistance, and portability as well as storage stability.

Example 17

Stick-Shaped Deodorant Composition
<Preparation>
A stick-shaped deodorant composition was prepared by step A of mixing ingredients 1 to 7 until uniform and heating at 95° C., step B of mixing ingredients 8 to 13 until uniform and heating at 85° C., and step C of adding B to A, emulsifying, adding ingredient 14, uniformly mixing, filling the emulsion into a stick container, and cooling.

| Formulation | % |
|---|---|
| 1. Partially crosslinked polyether-modified silicone composition*[1] | 4 |
| 2. Silicone/alkyl-branched, polyether-modified silicone*[2] | 1 |
| 3. Dimethylpolysiloxane (6cs) | 8 |
| 4. Neopentylglycol dicaprate | 8 |
| 5. Polymethylsilsesquioxane*[3] | 5 |
| 6. Polyethylene | 7 |
| 7. Paraffin | 2 |
| 8. Aluminum zirconium trichlorohydrex gly | 15 |
| 9. Butylene glycol | 5 |
| 10. Pentylene glycol | 2 |
| 11. Sodium citrate | 0.2 |
| 12. Sodium chloride | 0.5 |
| 13. Purified water | balance |
| 14. Fragrance | 0.03 |
| Total | 100.0 |

Total of component (A): 42%
Proportion of the sum of water and ethanol in component (A): 100%

*[1] Partially crosslinked polyether-modified silicone composition: KSG-210 (crosslinked part ~25%, dimethicone ~75%) from Shin-Etsu Chemical Co., Ltd.
*[2] Silicone/alkyl-branched, polyether-modified silicone: KF-6038 from Shin-Etsu Chemical Co., Ltd.
*[3] Polymethylsilsesquioxane: KMP-591 from Shin-Etsu Chemical Co., Ltd.

The resulting stick-shaped deodorant composition was found to have satisfactory feeling on use, extensibility, dry feeling, perspiration resistance, and portability as well as storage stability.

Example 18

Stick-Shaped Deodorant Composition
<Preparation>
A stick-shaped deodorant composition was prepared by step A of mixing ingredients 1 to 10 until uniform and heating at 95° C., step B of mixing ingredients 12 to 17 until uniform and heating at 85° C., and step C of adding B to A, emulsifying, adding ingredient 11, uniformly mixing, filling the emulsion into a stick container, and cooling.

| Formulation | % |
|---|---|
| 1. Partially crosslinked polyether-modified silicone composition*[1] | 4 |
| 2. Silicone/alkyl-branched, polyether-modified silicone*[2] | 1.5 |
| 3. Partially crosslinked dimethylpolysiloxane composition*[3] | 5 |
| 4. Dimethylpolysiloxane (2cs) | 2 |
| 5. Diphenylsiloxyphenyltrimethicone*[4] | 7 |
| 6. Tristrimethylsiloxymethylsilane*[5] | 5 |
| 7. Jojoba oil | 2 |
| 8. Poly(methyl methacrylate) | 2 |
| 9. Silica | 1 |
| 10. Ceresin | 9 |
| 11. Isopropylmethylphenol | 0.1 |
| 12. Aluminum hydrochloride | 10 |
| 13. Benzalkonium chloride | 0.2 |
| 14. Ethanol | 15 |
| 15. Phenoxyethanol | 0.3 |
| 16. Sodium citrate | 0.2 |
| 17. Magnesium sulfate | 1 |
| 18. Purified water | balance |
| Total | 100.0 |

Total of component (A): 55%
Proportion of the sum of water and ethanol in component (A): 90%

*[1] Partially crosslinked polyether-modified silicone composition: KSG-210 (crosslinked part ~25%, dimethicone ~75%) from Shin-Etsu Chemical Co., Ltd.
*[2] Silicone/alkyl-branched, polyether-modified silicone: KF-6038 from Shin-Etsu Chemical Co., Ltd.
*[3] Partially crosslinked dimethylpolysiloxane composition: KSG-16 (crosslinked part ~25%, cyclopentasiloxane ~75%) from Shin-Etsu Chemical Co., Ltd.
*[4] Diphenylsiloxyphenyltrimethicone: KF-56A from Shin-Etsu Chemical Co., Ltd.
*[5] Tristrimethylsiloxymethylsilane: TMF-1.5 from Shin-Etsu Chemical Co., Ltd.

The resulting stick-shaped deodorant composition was found to have satisfactory feeling on use, extensibility, dry feeling, perspiration resistance, and portability as well as storage stability.

The invention claimed is:
1. A water-in-oil emulsion type stick-shaped deodorant composition comprising
(A) 60 to 70% by weight of volatile component having a boiling point of up to 250° C.,
wherein component (A) contains water and ethanol, and the total of water and ethanol in component (A) is 90 to 100% by weight,
(B) either one of (B-1) an antiperspirant and (B-2) a bactericide, or a combination of (B-1) and (B-2),
(C) a crosslinked silicone surfactant selected from the group consisting of partially crosslinked polyether-modified silicones and partially crosslinked polyglycerol-modified silicones,
(D) a non-crosslinked silicone surfactant selected from the group consisting of linear or branched polyoxyethylene-modified organopolysiloxanes, linear or branched polyoxyethylene polyoxypropylene-modified organopolysiloxanes, linear or branched polyoxyethylene/alkyl-co-modified organopolysiloxanes, linear or branched polyoxyethylene polyoxypropylene/alkyl-co-modified organopolysiloxanes, linear or branched polyglycerol-modified organopolysiloxanes, and linear or branched polyglycerol/alkyl-co-modified organopolysiloxanes, and
(E) an oily component which is solid at 25° C.,
wherein the amount of component (B-1) blended is 0.1 to 30% by weight when it is used, the amount of component (B-2) blended is 0.05 to 2% by weight when it is used, the amount of component (C) blended is 0.15 to 3% by weight, and the amount of component (D) blended is 0.1 to 10% by weight, based on the deodorant composition.

2. The stick-shaped deodorant composition of claim 1 wherein component (B-1) is at least one antiperspirant selected from the group consisting of aluminum hydrochloride, allantoin aluminum hydrochloride, aluminum chloride, allantoin aluminum salt, tannic acid, persimmon tannin, aluminum potassium sulfate, zinc oxide, zinc p-phenol sulfonate, dry aluminum potassium sulfate, aluminum zirconium tetrachlorohydrate, and aluminum zirconium trichlorohydrex gly.

3. The stick-shaped deodorant composition of claim 1 wherein component (B-2) is at least one bactericide selected from the group consisting of triclosan, benzalkonium chloride, benzethonium chloride, chlorhexidine hydrochloride, chlorhexidine gluconate, cloflucarban, isopropyl methyl phenol, and salicylic acid.

4. The stick-shaped deodorant composition of claim 1 wherein component (E) is at least one oily component selected from the group consisting of carnauba wax, candelilla wax, rice wax, Japan wax, beeswax, spermaceti, solid paraffin, polyethylene, ceresin, ozokerite, microcrystalline wax, synthetic wax, stearyl alcohol, behenyl alcohol, cetanol, stearic acid, behenic acid, and silicone wax.

5. The stick-shaped deodorant composition of claim 1 wherein component (A) includes an oily volatile component selected from the group consisting of a dimethylpolysiloxane, an octamethyltetrasiloxane, a decamethylpentasiloxane, a dodecamethylhexasiloxane, a tristrimethylsiloxymethylsilane, a caprylyl methicone, a decamethylcyclopentasiloxane, a soft isoparaffin, an undecane, an isododecane, and mixtures thereof.

6. The stick-shaped deodorant composition of claim 1 wherein the total of water and ethanol in component (A) being 100% by weight.

7. The stick deodorant composition of claim 1, wherein the amount of component (B-1) blended is 0.1 to 20% by weight, based on the deodorant composition.

8. The stick deodorant composition of claim 1, wherein amount of component (C) blended is 0.2 to 2.5% by weight, based on the deodorant composition.

9. The stick deodorant composition of claim 1, wherein the component (D) is a non-crosslinked branched silicone surfactant.

* * * * *

UNITED STATES PATENT AND TRADEMARK OFFICE
CERTIFICATE OF CORRECTION

PATENT NO. : 11,547,643 B2  
APPLICATION NO. : 16/643005  
DATED : January 10, 2023  
INVENTOR(S) : Masayuki Konishi et al.

It is certified that error appears in the above-identified patent and that said Letters Patent is hereby corrected as shown below:

On the Title Page

Item (73), Assignee, Change:  
"SHTN-ETSU CHEMICAL CO., LTD., Tokyo (JP)"  
To:  
--SHIN-ETSU CHEMICAL CO., LTD., Tokyo (JP)--

Signed and Sealed this  
Fourth Day of July, 2023

Katherine Kelly Vidal  
*Director of the United States Patent and Trademark Office*